US 6,363,932 B1

(12) United States Patent
Forchione et al.

(10) Patent No.: US 6,363,932 B1
(45) Date of Patent: Apr. 2, 2002

(54) AEROSOL ENHANCEMENT DEVICE

(75) Inventors: Dennis Forchione, Brecksville, OH (US); Robert Johnson, Yucca Valley, CA (US)

(73) Assignee: Clinical Technologies, Inc., Broadview Heights, OH (US)

( * ) Notice: Subject to any disclaimer, the term of this patent is extended or adjusted under 35 U.S.C. 154(b) by 0 days.

(21) Appl. No.: 09/610,801

(22) Filed: Jul. 6, 2000

(51) Int. Cl.$^7$ .............................................. A61M 16/00
(52) U.S. Cl. ............................. 128/203.12; 128/200.14
(58) Field of Search ..................... 128/200.14, 200.18, 128/200.21, 203.12, 203.15, 200.24; 239/203.21, 335, 338, 354

(56) References Cited

U.S. PATENT DOCUMENTS

| 3,762,409 A | 10/1973 | Lester |
| 3,769,973 A | 11/1973 | Esbenshade, Jr. |
| 3,826,255 A | 7/1974 | Havstad et al. |
| 4,007,238 A | 2/1977 | Glenn |
| 4,061,698 A | 12/1977 | Thornwald |
| 4,094,317 A | 6/1978 | Wasnich |
| 4,100,235 A | 7/1978 | Thornwald |
| 4,113,809 A | 9/1978 | Abair et al. |
| 4,210,155 A | 7/1980 | Grimes |
| 4,231,973 A | 11/1980 | Young et al. |
| 4,253,468 A | 3/1981 | Lehmbeck |
| 4,259,951 A | 4/1981 | Chernack et al. |
| 4,268,460 A | 5/1981 | Boiarski et al. |
| 4,396,015 A | 8/1983 | Johnson |
| 4,534,343 A | 8/1985 | Nowacki et al. |
| 4,560,519 A | 12/1985 | Cerny |
| 4,657,007 A | 4/1987 | Carlin et al. |
| 4,660,547 A | 4/1987 | Kremer, Jr. |
| 4,823,784 A | 4/1989 | Bordoni et al. |
| 4,911,157 A | 3/1990 | Miller |
| 4,938,209 A | 7/1990 | Fry |

(List continued on next page.)

Primary Examiner—John G. Weiss
Assistant Examiner—Teena Mitchell
(74) Attorney, Agent, or Firm—Stout, Uxa, Buyan & Mullins, LLP; Donald E. Stout

(57) ABSTRACT

An aerosol medication delivery apparatus includes a fixed volume holding chamber which is constructed to allow for a uniformly mixed, concentrated bolus of medicated aerosol to be delivered with each breath. The device further includes a universal inlet, so that any standard small volume nebulizer, as well as any standard metered dose inhaler (MDI), may be utilized therewith. Also filtration can be added to address contaminated patient air and aerosol. A one-way valve is positioned between the holding chamber and a tee piece for attaching the holding chamber to a patient mouthpiece, to help control the loss of aerosol, and thereby reduce waste. The device is simply constructed of two molded plastic members, which are readily engaged to complete its assembly.

39 Claims, 4 Drawing Sheets

U.S. PATENT DOCUMENTS

| | | |
|---|---|---|
| 4,951,661 A | 8/1990 | Sladek |
| 5,020,530 A | 6/1991 | Miller |
| RE33,642 E | 7/1991 | Lester |
| 5,027,809 A | 7/1991 | Robinson |
| 5,036,840 A | 8/1991 | Wallace |
| 5,062,419 A | 11/1991 | Rider |
| 5,086,765 A | 2/1992 | Levine |
| 5,099,833 A | 3/1992 | Michaels |
| 5,170,782 A | 12/1992 | Kocinski |
| 5,178,138 A | 1/1993 | Walstrom et al. |
| 5,209,225 A | 5/1993 | Glenn |
| 5,235,969 A | 8/1993 | Bellm |
| 5,241,954 A | 9/1993 | Glenn |
| 5,277,175 A | 1/1994 | Riggs et al. |
| 5,287,847 A | 2/1994 | Piper et al. |
| 5,297,543 A * | 3/1994 | Larson et al. .......... 128/200.23 |
| 5,299,565 A | 4/1994 | Brown |
| 5,357,945 A | 10/1994 | Messina |
| 5,379,760 A | 1/1995 | Ryder |
| 5,388,571 A | 2/1995 | Roberts et al. |
| 5,396,883 A | 3/1995 | Knupp et al. |
| 5,415,161 A | 5/1995 | Ryder |
| 5,431,154 A | 7/1995 | Seigel et al. |
| 5,458,135 A | 10/1995 | Patton et al. |
| 5,477,849 A | 12/1995 | Fry |
| 5,479,920 A | 1/1996 | Piper et al. |
| 5,503,139 A | 4/1996 | McMahon et al. |
| 5,513,626 A | 5/1996 | Hamilton |
| 5,520,167 A | 5/1996 | Hamilton |
| 5,546,930 A | 8/1996 | Wikefeldt |
| 5,570,682 A | 11/1996 | Johnson |
| 5,579,757 A | 12/1996 | McMahon et al. |
| 5,584,285 A | 12/1996 | Salter et al. |
| 5,586,551 A | 12/1996 | Hilliard |
| 5,596,982 A | 1/1997 | Blaha-Schnabel |
| 5,598,835 A | 2/1997 | von Schrader |
| 5,613,489 A | 3/1997 | Miller et al. |
| 5,653,223 A | 8/1997 | Pruitt |
| 5,685,291 A | 11/1997 | Marsh |
| 5,704,344 A | 1/1998 | Cole |
| 5,727,542 A | 3/1998 | King |
| 5,738,086 A | 4/1998 | McMahon et al. |
| 5,752,502 A | 5/1998 | King |
| 5,775,320 A | 7/1998 | Patton et al. |
| 5,782,232 A | 7/1998 | Rowland |
| 5,797,389 A | 8/1998 | Ryder |
| 5,823,179 A * | 10/1998 | Grychowski et al. .. 128/200.18 |
| 5,988,162 A * | 11/1999 | Retallick, III .......... 128/203.12 |
| 6,014,972 A * | 1/2000 | Sladek .................. 128/203.12 |
| 6,085,741 A * | 7/2000 | Becket .................. 128/200.21 |
| 6,116,233 A * | 9/2000 | Denyer et al. ......... 128/200.18 |
| 6,138,668 A * | 10/2000 | Patton et al. .......... 128/200.14 |
| 6,223,745 B1 * | 5/2001 | Hammarlund et al. . 128/200.18 |

* cited by examiner

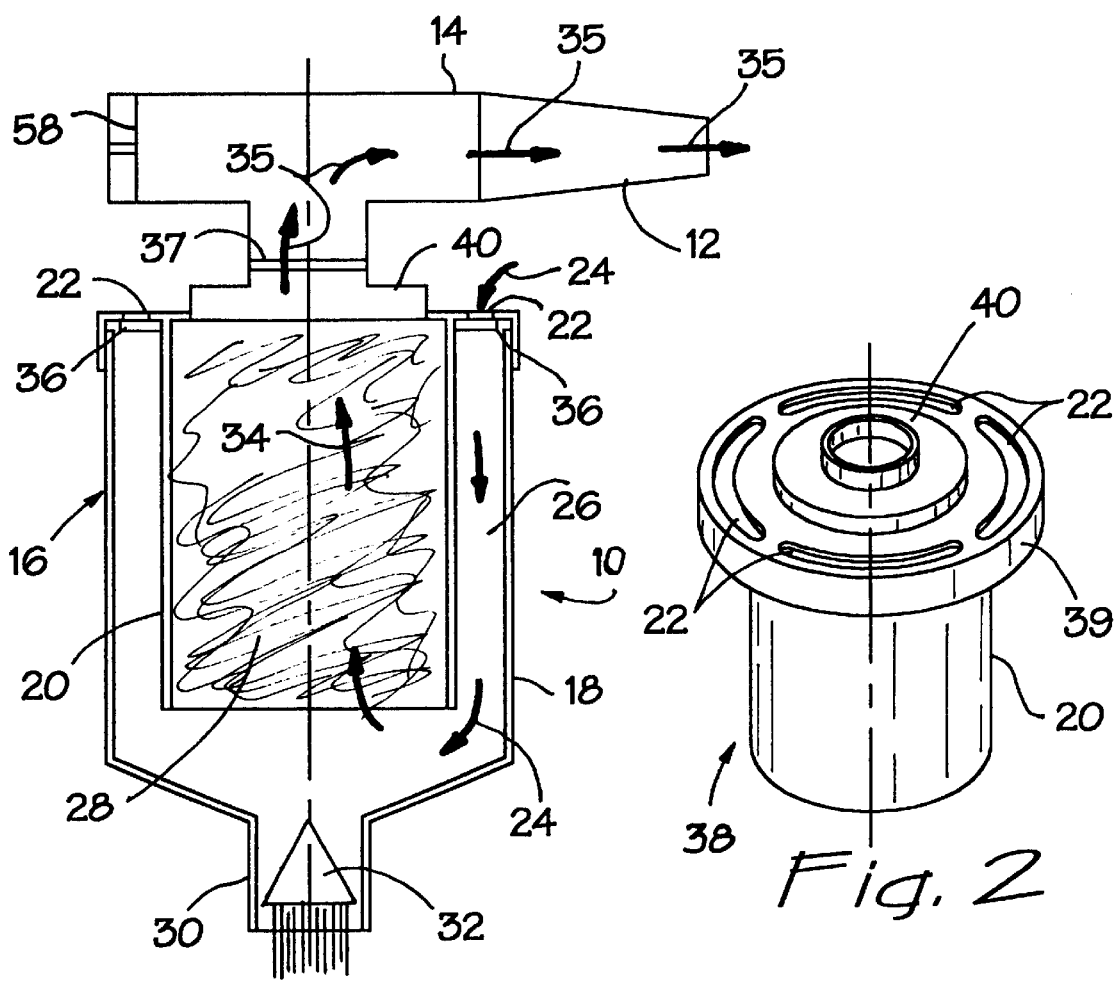
Fig. 1
Fig. 2
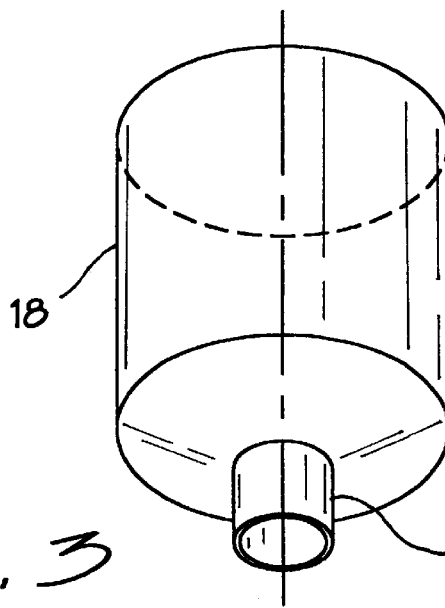
Fig. 3

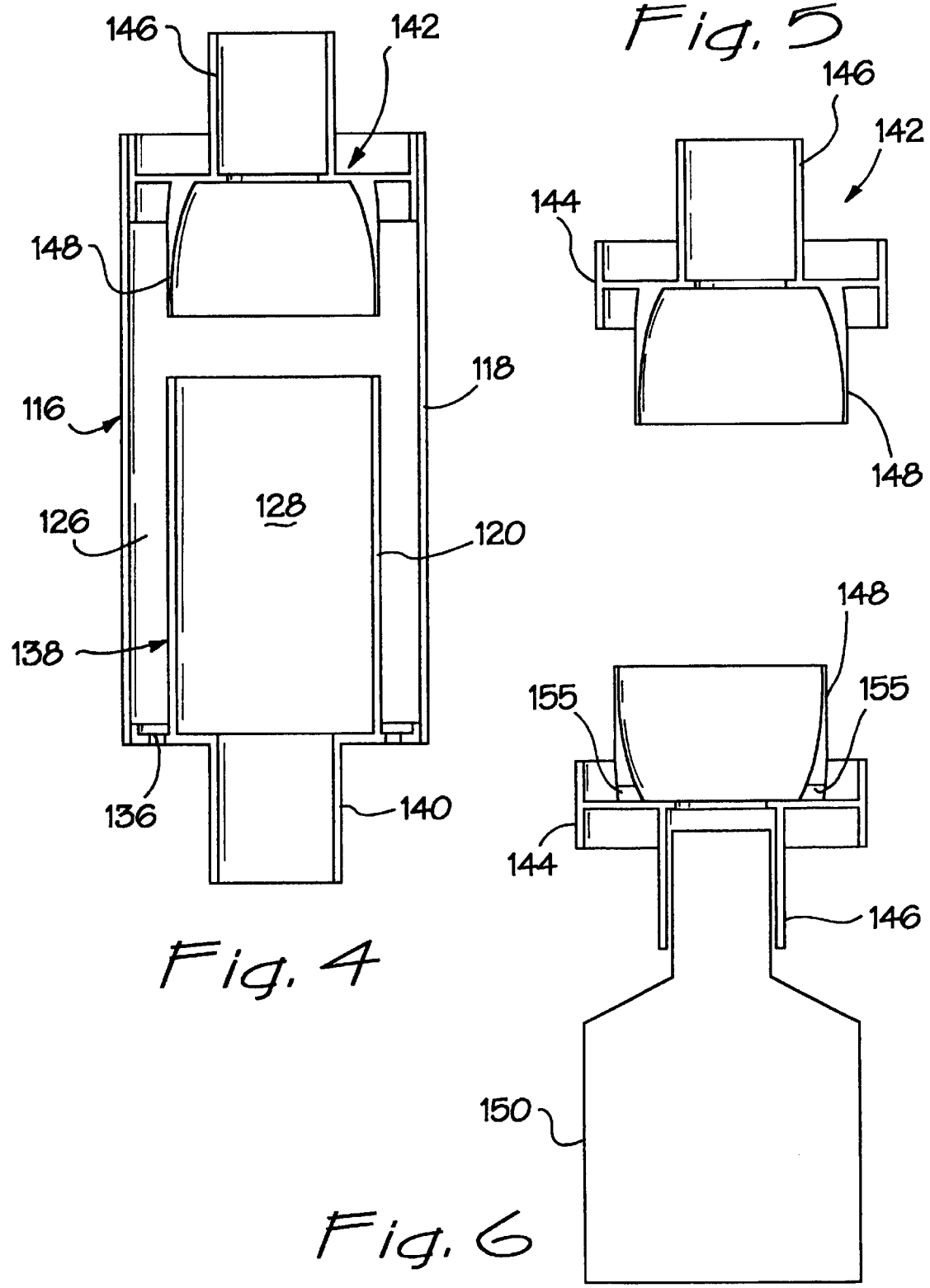

AEROSOL ENHANCEMENT DEVICE

BACKGROUND OF THE INVENTION

This invention relates generally to an improved aerosol inhalation device, and more particularly to an aerosol enhancement device which is usable in combination with both a nebulizer and a metered dose inhaler.

Aerosol inhalation devices, for the purpose of delivering medication, entrained in an aerosol spray, to a patient using inhalation therapy, as an alternative to oral medications such as capsules or pills, or to injected medications, are well known in the art. For example, U.S. Pat. No. 4,210,155 to Grimes is representative of the prior art. In the Grimes patent there is disclosed a fixed volume mist accumulation chamber for use in combination with a nebulizer and a tee connection of an inhalation conduit for accumulating medicated mist and facilitating its delivery to a patient.

However, the Grimes device, as is typical for prior art devices, is plagued with problems typical of such devices. These problems include, for example, non-uniform concentrations of medication, resulting in difficulties in regulating patient dosage, and significant waste of medication. Additionally, the Grimes device is relatively complex, so that it is expensive to manufacture and difficult to use.

Many other such devices are available which do not include a mixing chamber. In other words, the nebulizer is attached directly to the aforementioned tee connection. Of course, such devices are even less suited to satisfactory regulation of the medication being delivered to the patient than the Grimes device, because there is substantially no ability to uniformly mix the medication with entrained fluid, such as air, before delivery to the mouthpiece on which the patient is inhaling.

In addition to nebulizers, metered dose inhalers (MDI) are also available for delivering a medicated aerosol to a patient. These MDI devices differ from nebulizers primarily in that a propellant is used to deliver the medication.

It would be advantageous to have an aerosol medication delivery device which included a mixing chamber between the medication delivery apparatus and the mouthpiece, wherein the medication could be uniformly mixed with entrained air in an improved manner over that achieved by the Grimes patent apparatus. It would also be beneficial for such a device to be simple to manufacture and assemble, and easy to use. Finally, if such a device could be made universally adaptable for use with any known nebulizer on the market, as well as with MDI's, this would be a great advance in the art.

SUMMARY OF THE INVENTION

The present invention provides an aerosol medication delivery apparatus which incorporates the aforementioned advantages. The inventive device includes a fixed volume holding chamber which is constructed to allow for a uniformly mixed, concentrated bolus of medicated aerosol to be delivered with each breath. The device further includes a universal inlet, so that any standard small volume nebulizer, as well as any standard MDI, may be utilized therewith. Also filtration can be added to address contaminated patient air and aerosol. A one-way valve is positioned between the holding chamber and a tee piece for attaching the holding chamber to a patient mouthpiece, to help control the loss of aerosol, and thereby reduce waste. The device is simply constructed of two molded plastic members, which are readily engaged to complete its assembly.

More particularly, an aerosol enhancement device is provided which comprises a mouthpiece and a tower member fluidly attached to the mouthpiece. The tower member has an outer body which defines an interior volume, together with an inner wall disposed in the outer body. The inner wall extends a substantial distance through the interior volume and defines a holding chamber interiorly of the inner wall. An annular air passage is defined between the inner wall and the outer body. An inlet port is disposed in the tower member for receiving a medicated aerosol from an exterior source into the holding chamber. An air inlet port is disposed in the tower member, as well, for receiving air into the air passage. Advantageously, because of the lengthy inner wall, which may preferably comprise a tubular member, so that the resultant defined air passage is annular, the air in the air passage flows around said inner wall and into holding chamber, to be entrained with the medicated aerosol for a sufficient distance as it travels through the holding chamber to ensure thorough mixing.

A further innovation in the aforementioned device is the employment of a T-piece for attachment of the tower member to the mouthpiece, and the incorporation of a one-way valve in the T-piece for preventing medication waste. A one-way valve, preferably comprising an O-ring valve, is preferably disposed in the air inlet port, as well.

In another aspect of the invention, an aerosol enhancement device is provided which comprises a mouthpiece and a tower member fluidly attached to the mouthpiece. The tower member has an outer body which defines an interior volume. An inlet port is disposed in the tower member for receiving a medicated aerosol from an exterior source into the interior volume. Advantageously, an adapter is disposed in the medicated aerosol inlet port. The inventive adapter comprises a universal fitting which is capable of attaching the tower member to either a nebulizer or a metered dose inhaler (MDI).

Preferably, the inventive adapter is reversible, being disposable in a first orientation for attachment of the tower member to a nebulizer, and being disposable in a second orientation for attachment of the tower member to an MDI. In its preferred configuration, the universal adapter comprises a first rigid connector end and a second flexible connector end, the first rigid connector end being adapted for attachment to a nebulizer and the second flexible connector end being adapted for attachment to an MDI. The adapter preferably further comprises a flange portion for engaging the adapter with the tower member.

In still another aspect of the invention, an aerosol enhancement device is provided which comprises a mouthpiece and a T-piece attached to the mouthpiece. The T-piece has a first port for attachment to the mouthpiece, a second port which is open to atmosphere, and a third port. A medication dispenser is attached to the third port, and, advantageously, an exhalation filter is disposed in the second port.

In yet another aspect of the invention, a tower member is provided which is usable with a mouthpiece, for dispensing medicated aerosol to a patient. The inventive tower member comprises an outer body which defines an interior volume, and an an inner wall disposed in the outer body. The inner wall extends a substantial distance through the interior volume and defines a holding chamber which is disposed interiorly of the inner wall. The inner wall and the outer body define an air passage therebetween. An inlet port is disposed in the tower member for receiving a medicated aerosol from an exterior source, such as a nebulizer or MDI, into the holding chamber, and an air inlet port is disposed in the tower member for receiving air into the air passage. An outlet port for dispensing medicated aerosol entrained in air from the holding chamber to the mouthpiece is provided as well, wherein the air in the air passage flows therethrough around the inner wall and into the holding chamber, to be entrained with the medicated aerosol.

In another aspect of the invention, there is provided a tower member usable with a mouthpiece, for dispensing medicated aerosol to a patient. The tower member comprises an outer body which defines an interior volume, and an inlet port disposed in the tower member outer body for receiving a medicated aerosol from an exterior source into the interior volume. An adapter is disposed in the medicated aerosol inlet port. The adapter comprises a universal fitting which is advantageously capable of attaching the tower member to either a nebulizer or a metered dose inhaler (MDI).

In yet another aspect of the invention, there is provided a tower member usable with a mouthpiece, for dispensing medicated aerosol to a patient. The tower member comprises a first member comprising a fitting for attachment of the tower member to the mouthpiece and a disk having an air inlet port disposed therein, as well as a second member comprising an outer body which defines an interior volume and an inlet port disposed in the tower member outer body for receiving a medicated aerosol from an exterior source into the interior volume. Advantageously, a medicated aerosol delivery device is easily assembled by engaging the first and second members to form the aforementioned tower member.

In still another aspect of the invention, there is provided a tower member usable with a mouthpiece, for dispensing medicated aerosol to a patient. The tower member comprises an outer body which defines an interior volume, and an inlet port disposed in the tower member outer body for receiving a medicated aerosol from an exterior source, which is preferably a nebulizer, into the interior volume. An adapter is disposed in the medicated aerosol inlet port, and comprises a fitting which is capable of attaching the tower member to the exterior source. Advantageously, a drainage channel, and preferably four spaced drainage channels, is/are disposed near a joint between the fitting and the outer body for draining liquid from the interior volume into the exterior source.

The invention, together with additional features and advantages thereof, may best be understood by reference to the following description taken in conjunction with the accompanying illustrative drawing.

BRIEF DESCRIPTION OF THE DRAWINGS

FIG. 1 is a side plan view of one embodiment of the inventive aerosol enhancement device;

FIG. 2 is a perspective view of the top portion of the two-piece holding chamber which forms a part of the aerosol enhancement device illustrated in FIG. 1;

FIG. 3 is a perspective view of the bottom portion of the two-piece holding chamber which forms a part of the aerosol enhancement device illustrated in FIG. 1;

FIG. 4 is a side plan view of the holding chamber of a modified embodiment of the inventive aerosol enhancement device;

FIG. 5 is a side plan view of a reversible fitting, in isolation, which forms a portion of the holding chamber illustrated in FIG. 4, which in one orientation adapts the holding chamber for attachment to a nebulizer, and in a second orientation adapts the holding chamber for attachment to a metered dose inhaler;

FIG. 6 is a side plan view of the reversible fitting illustrated in FIG. 5, attached to a nebulizer;

DESCRIPTION OF THE PREFERRED EMBODIMENT

Figure 8:
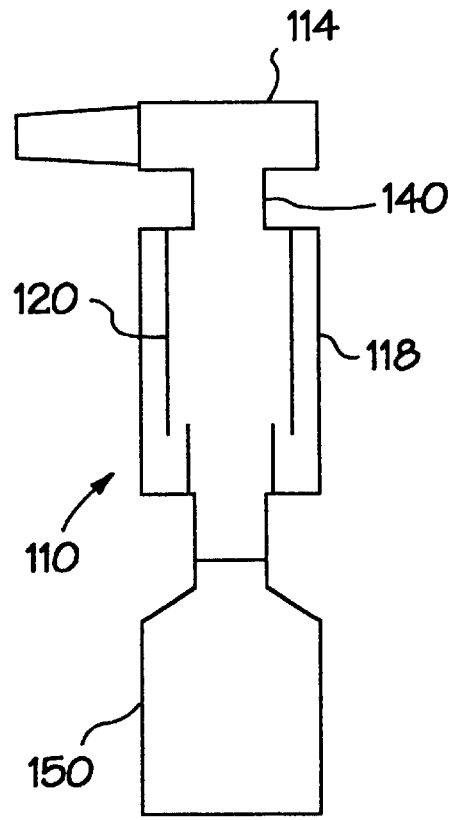
FIG. 8 is a side plan view of an entire inhalation system constructed in accordance with the principles of the present invention, wherein the holding chamber is attached to a nebulizer.

Referring now more particularly to FIGS. 1–3, there is shown a first embodiment of the inventive aerosol enhancement device 10. The device 10 comprises a mouthpiece 12 which is fluidly connected with a T-piece 14. The T-piece 14 is, in turn, attached to a tower 16. The tower 16 comprises an outer body 18 and inner tubing 20. As will be described in more detail below, air is entrained into the outer body 18 through air inlet ports 22, as shown by arrows 24, traveling through an annular passage 26 which is defined by the outer walls of the tower 16 and the inner tubing 20. When the air reaches the lower edge of the inner tubing 20, it reverses direction and travels upwardly into a holding chamber 28, which is defined by the inner tubing 20. A lower inlet port 30 supplies a medicated aerosol, as shown by arrow 32, into the holding chamber 28, which functions as a mixing zone for mixing the incoming medication with the incoming air.

As noted supra, the purpose for the holding chamber 28 is to thoroughly mix the incoming medication and air together, which occurs as the two components flow upwardly together, in turbulent fashion, through the holding chamber 28, as shown by arrow 34. Once thoroughly mixed, the medicated mixture flows into the T-piece 14, and then into the mouthpiece 12 for inhalation by a patient, as shown by arrows 35.

A valve, preferably an o-ring valve 36, controls the air inflow through each air inlet port 22, in a manner to be described more fully below, as shown in FIG. 1. A second check valve 37 is preferably disposed in the vicinity of the fitting 40, between the chamber 28 and the T-piece 14, for the purpose of controlling the loss of aerosol.

Referring now particularly to FIGS. 2 and 3, it is apparent that the outer body 18 is preferably formed as a single piece with the lower inlet port 30 (FIG. 3). Additionally, the inner tube 20 is preferably formed as a single piece 38 with a disk 39 which includes a plurality of the air inlet ports 22, together with a fitting 40 for attachment to the T-piece 14. The two pieces 18 and 38 are engaged by inserting the single piece 38 into the outer body 18, as shown in FIG. 1, to form the device 10.

Now with reference to FIGS. 4–9, a modified embodiment of the inventive device is illustrated, wherein like elements are designated by like reference numerals, preceded by the numeral 1. In this embodiment, the construction of the device 110 is similar to that of the device 10 in FIGS. 1–3, except for the employment of a reversible fitting or adapter 142 in place of the fixed inlet port 30 in the prior embodiment. The adaptive fitting 142 includes an engagement flange 144, a rigid connector end 146, and a flexible connector end 148. The flexible connector end 148 is preferably in the nature of a boot, fabricated of a soft pliable material, such as Neoprene, while the engagement flange 144 and rigid connector end 146 are preferably fabricated of a rigid molded plastic, such as ABS, which may be the same material that is used to fabricate the remainder of the device. An injection molding process may be used to mold the device, if desired.

Figure 9:
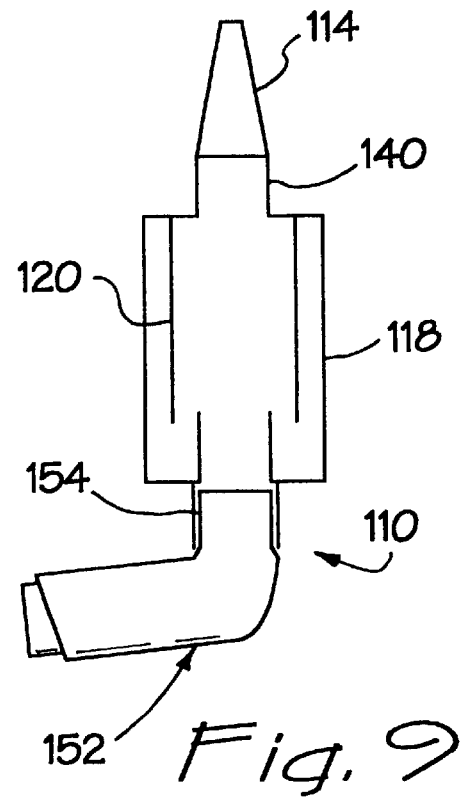
FIG. 9 is a side plan view of an entire inhalation system constructed in accordance with the principles of the present invention, wherein the holding chamber is attached to a metered dose inhaler.
Figure 7:
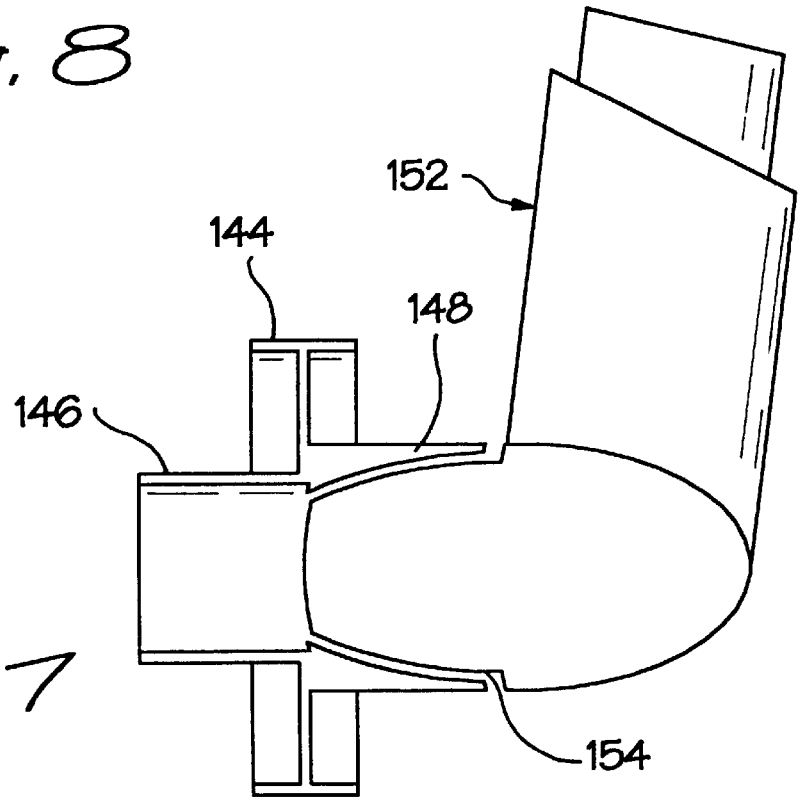
FIG. 7 is a side plan view of the reversible fitting illustrated in FIG. 5, attached to a metered dose inhaler.

The purpose of the adaptive fitting 142 is to permit the tower body 118 to be able to accommodate attachment of the device to both a nebulizer 150 and a Metered Dose Inhaler (MDI) 152 (see FIGS. 8 and 9). As is shown in FIGS. 6 and 8, the smaller, rigid connector end 146 may be used to attach the device 110 to a nebulizer 150. On the other hand, an MDI typically has a non-round mouthpiece 154, and therefore the inventors have found that a pliable boot connector such as connector 148 is required for a successful fit, by providing a flared access for the MDI boot, as shown in FIGS. 7 and 9.

The inventors have found that when the inventive apparatus is in the "nebulizer mode", as shown in FIG. 6, for example, it is particularly advantageous to include drain channels 155 in the flexible connector end 148 of the adaptive fitting 142. In a preferred configuration, the channels are disposed in the connector end 148, just above the joint between the connector end and the floor of the tower 116. Preferably, four such channels, spaced equally about the circumference of the flexible connector end 148, are employed, though other arrangements, including a different number of channels, or an annular channel, could be employed, if desired. The purpose for the drain channels 155 is to re-capture liquid medication which may accumulate in the tower 116 as a result of incomplete entrainment of the medication in the air flow which enters the tower 116 through the air inlets 136 and advances into the holding chamber 128 for inhalation by the patient. The re-captured medication flows through the drain channels 155 back into the nebulizer 150, where it can be administered to the patient.

Of course, while, for exemplary purposes, the drain channels 155 are illustrated only in the FIGS. 4–9 embodiment, such channels, or other drainage means, could be employed in any of the illustrated embodiments, or other embodiments incorporating the unique features of the present invention, as well.

Figure 10:
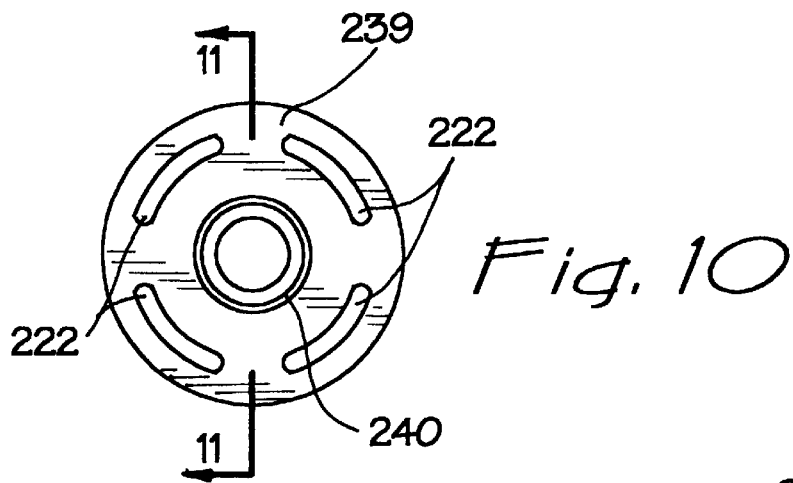
FIG. 10 is a top view of a third modified embodiment of the inventive aerosol enhancement device.
Figure 11:
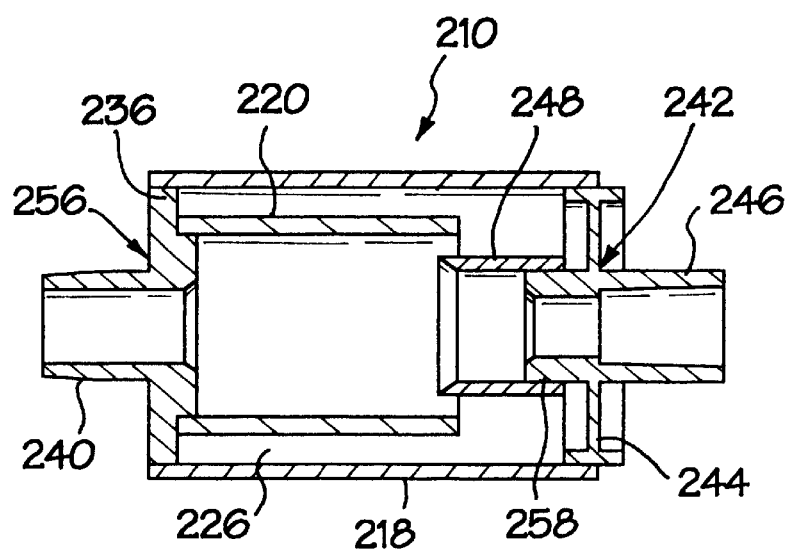
FIG. 11 is a cross-sectional view taken along lines 11—11 in FIG. 10.
Figure 12:
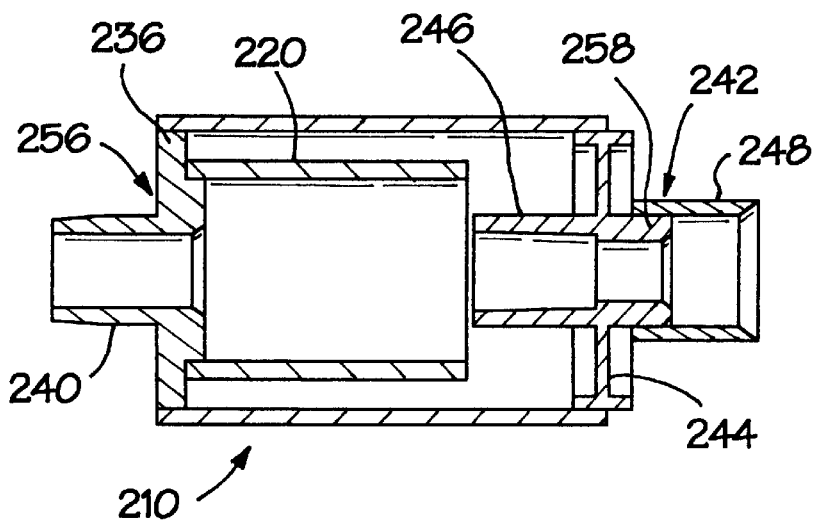
FIG. 12 is a cross-sectional view similar to that of FIG. 11, wherein the reversible fitting is shown in its alternate orientation.

Now with reference to FIGS. 10–12, there is shown yet another presently preferred embodiment of the inventive aerosol enhancement device. In this embodiment, wherein like elements to those of previous embodiments are designated by like reference numerals, preceded by the numeral 2, which is substantially similar to the embodiment of FIGS. 4–9, the only substantial difference is in the employment of an end cap 256, which includes the fitting 240 and the disk 239. The end cap 256 is not unitary with the inner tube 220, however, as in the preceding embodiment. Additionally, as is seen in FIGS. 11 and 12, the flexible connector end 248 is attached to the rigid connector end 246 by means of an annular flanged joint 258. Of course, FIGS. 11 and 12 are similar, except that the reversible fitting 242 is oriented in an opposite manner in FIG. 12 with respect to its orientation in FIG. 11, for the purpose of accommodating an MDI, rather than a nebulizer.

Presently preferred design options include holding chamber volumes ranging from 90 cc to 140 cc, and chamber lengths ranging from 2.95 inches to 1.56 inches, depending upon the chamber volume and the internal diameter of the chamber. The total stacked height of the inventive apparatus, including an attached nebulizer, may range from 6.7 to 8.3 inches in the presently preferred embodiments, depending upon chamber volume and internal diameter.

In operation, in any of the illustrated embodiments, the apparatus 10 is particularly adapted for dual use applications, as noted supra. In particular, the device 10 may be utilized in conjunction with a nebulizer, wherein the tower 16, and in particular, the holding chamber 28, functions to recirculate medication introduced by the nebulizer, in order to provide a denser application of medication to the patient. The provided fittings are universally suitable for attachment to any known nebulizer. In an alternative configuration, wherein the device 10 is utilized in conjunction with an MDI, the tower 16 functions as a spacer, for the purpose of ensuring a more uniformly mixed dose of medication to the patient.

Whether The device 10, 110, 210 is being used with a nebulizer or an MDI, the purpose of the holding chamber 28 is to repeatedly capture the generated aerosol from the nebulizer or MDI into the fixed volume chamber, which allows for a concentrated bolus of medicated aerosol to be delivered with each breath taken by a patient who is breathing through the mouthpiece 12. In the case of a nebulizer 150, the medicated aerosol is drawn therefrom by the vacuum created by inspiration by the patient through the mouthpiece, while in the case of an MDI, a propellant injects the medicated aerosol therefrom into the chamber 28. The inventors have advantageously found that the length of the inner holding chamber 28 in each embodiment (i.e. the length of the inner tubing 20) should be more than half of the length of the tower 18, and preferably much more than half, in order to ensure adequate entrainment and mixing of the air and medicated aerosol. Though not shown, in some embodiments, a bridge adapter may be employed to adapt the device to various prior art mouthpieces. Also, the inventors have found that an exhalation filter 58 (FIG. 1) disposed in the exit end of the T-piece 14, is useful in dealing with circumstances involving contaminated or infectious patient air and aerosol, to minimize the spread of infection.

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An aerosol enhancement device, comprising:
   a mouthpiece;
   a tower member fluidly attached to said mouthpiece, said tower member having an outer body which defines an interior volume;
   an inner wall disposed in said outer body, said inner wall extending a substantial distance through said interior volume and defining a holding chamber interiorly of said inner wall, said inner wall and said outer body defining an air passage therebetween;

an inlet port disposed in said tower member for receiving a medicated aerosol from an exterior source into said holding chamber;

an air inlet port disposed in said tower member for receiving air into said air passage; and a T-piece for connecting said mouthpiece to said tower member;

wherein the air in said air passage flows therethrough around said inner wall and into said holding chamber, to be entrained with said medicated aerosol.

2. The aerosol enhancement device as recited in claim 1, and further comprising a one-way valve in said T-piece.

3. The aerosol enhancement device as recited in claim 1, and further comprising an outlet port in said T-piece which is open to atmosphere, said outlet port having an exhalation filter disposed therein.

4. The aerosol enhancement device as recited in claim 1, wherein said inner wall comprises a tubular member.

5. The aerosol enhancement device as recited in claim 1, and further comprising a one-way valve disposed in said air inlet port.

6. The aerosol enhancement device as recited in claim 5, wherein said one-way valve comprises an O-ring valve.

7. The aerosol enhancement device as recited in claim 1, and further comprising an adapter disposed in said medicated aerosol inlet port, said adapter comprising a universal fitting which is capable of attaching said tower member to either a nebulizer or a metered dose inhaler (MDI).

8. The aerosol enhancement device as recited in claim 7, wherein said adapter is reversible, being disposable in a first orientation for attachment of said tower member to a nebulizer, and being disposable in a second orientation for attachment of said tower member to an MDI.

9. The aerosol enhancement device as recited in claim 8, wherein said adapter comprises a first rigid connector end and a second flexible connector end, said first rigid connector end being adapted for attachment to a nebulizer and said second flexible connector end being adapted for attachment to an MDI.

10. The aerosol enhancement device as recited in claim 9, said adapter further comprising a flange portion for engaging said adapter with said tower member.

11. The aerosol enhancement device as recited in claim 9, and further comprising a drainage channel disposed in said second flexible connector end, for draining liquid from said tower member to a nebulizer connected to said first rigid connector end.

12. The aerosol enhancement device as recited in claim 1, wherein said air inlet port is disposed on a disk which is attached to said inner wall.

13. The aerosol enhancement device as recited in claim 12, wherein said disk, said inner wall, and said T-piece are all molded as an integral unit.

14. The aerosol enhancement device as recited in claim 12, wherein said disk and said T-piece comprise an integral end cap which is attachable to said tower member.

15. The aerosol enhancement device as recited in claim 1, wherein said outer body has a total length, and said inner wall extends more than half of said total length through said interior volume.

16. An aerosol enhancement device, comprising:

a mouthpiece;

a tower member fluidly attached to said mouthpiece, said tower member having an outer body which defines an interior volume;

an inlet port disposed in said tower member for receiving a medicated aerosol from an exterior source into said interior volume; and an adapter disposed in said medicated aerosol inlet port, said adapter comprising a universal fitting which is capable of attaching said tower member to either a nebulizer or a metered dose inhaler (MDI).

17. The aerosol enhancement device as recited in claim 16, and further comprising a drainage channel disposed in said universal fitting, for draining liquid from said tower member to a nebulizer attached thereto by means of said fitting.

18. The aerosol enhancement device as recited in claim 16, wherein said adapter is reversible, being disposable in a first orientation for attachment of said tower member to a nebulizer, and being disposable in a second orientation for attachment of said tower member to an MDI.

19. The aerosol enhancement device as recited in claim 18, wherein said adapter comprises a first rigid connector end and a second flexible connector end, said first rigid connector end being adapted for attachment to a nebulizer and said second flexible connector end being adapted for attachment to an MDI.

20. The aerosol enhancement device as recited in claim 20, said adapter further comprising a flange portion for engaging said adapter with said tower member.

21. A tower member usable with a mouthpiece, for dispensing medicated aerosol to a patient, said tower member comprising:

an outer body which defines an interior volume;

an inner wall disposed in said outer body, said inner wall extending a substantial distance through said interior volume and defining a holding chamber interiorly of said inner wall, said inner wall and said outer body defining an air passage therebetween;

an inlet port disposed in said tower member for receiving a medicated aerosol from an exterior source into said holding chamber;

an air inlet port disposed in an upper portion of said tower member and adjacent to an upper portion of said inner wall for receiving air into said air passage; and an outlet port for dispensing medicated aerosol entrained in air from said holding chamber to said mouthpiece;

wherein the air in said air passage flows therethrough around said inner wall and into said holding chamber, to be entrained with said medicated aerosol.

22. The tower member as recited in claim 21, wherein there is no pressurized air inlet for supplying pressurized air to said holding chamber.

23. A tower member usable with a mouthpiece, for dispensing medicated aerosol to a patient, said tower member comprising:

an outer body which defines an interior volume;

an inlet port disposed in said tower member outer body for receiving a medicated aerosol from an exterior source into said interior volume; and an adapter disposed in said medicated aerosol inlet port, said adapter comprising a universal fitting which is capable of attaching said tower member to either a nebulizer or a metered dose inhaler (MDI).

24. The tower member as recited in claim 23, wherein said adapter is reversible, being disposable in a first orientation for attachment of said tower member to a nebulizer, and being disposable in a second orientation for attachment of said tower member to an MDI.

25. The tower member as recited in claim 24, wherein said adapter comprises a first rigid connector end and a second flexible connector end, said first rigid connector end being adapted for attachment to a nebulizer and said second flexible connector end being adapted for attachment to an MDI.

26. The tower member as recited in claim 25, said adapter further comprising a flange portion for engaging said adapter with said tower member.

27. A tower member usable with a mouthpiece, for dispensing medicated aerosol to a patient, said tower member comprising:

a first member comprising a fitting for attachment of said tower member to said mouthpiece and a disk having an air inlet port disposed therein; and a second member comprising an outer body which defines an interior volume and an inlet port disposed in said tower member outer body for receiving a medicated aerosol from an exterior source into said interior volume;

wherein said first and second members are engageable to form said tower member.

28. The tower member as recited in claim 27, wherein said first member is constructed of molded plastic.

29. The tower member as recited in claim 27, wherein said second member is constructed of molded plastic.

30. The tower member as recited in claim 27, said first member comprising an end cap insertable into said second member.

31. The tower member as recited in claim 21, wherein said first member further includes an inner wall which extends downwardly into said outer body when said first and second members are engaged, thereby defining a holding chamber therewithin, and an air passage between said outer wall and said inner wall.

32. The tower member as recited in claim 31, wherein said inner wall comprises a tubular wall, so that the defined air passage is annular.

33. A tower member usable with a mouthpiece, for dispensing medicated aerosol to a patient, said tower member comprising:

an outer body which defines an interior volume;

an inlet port disposed in said tower member outer body for receiving a medicated aerosol from an exterior source into said interior volume;

an adapter disposed in said medicated aerosol inlet port, said adapter comprising a fitting which is capable of attaching said tower member to said exterior source; and a drainage channel disposed near a joint between said fitting and said outer body for draining liquid from said interior volume into said exterior source.

34. The tower member as recited in claim 33, and further comprising a plurality of said drainage channels, spaced about a periphery of said joint between said fitting and said outer body.

35. The tower member as recited in claim 33, wherein said exterior source comprises a nebulizer.

36. An aerosol enhancement device, comprising:

a mouthpiece;

a tower member fluidly attached to said mouthpiece, said tower member having an outer body which defines an interior volume;

an inner wall disposed in said outer body, said inner wall extending a substantial distance through said interior volume and defining a holding chamber interiorly of said inner wall, said inner wall and said outer body defining an air passage therebetween;

an inlet port disposed in said tower member for receiving a medicated aerosol from an exterior source into said holding chamber;

an air inlet port disposed in said tower member for receiving air into said air passage; and a one-way valve disposed in said air inlet port;

wherein the air in said air passage flows therethrough around said inner wall and into said holding chamber, to be entrained with said medicated aerosol.

37. An aerosol enhancement device, comprising:

a mouthpiece;

a tower member fluidly attached to said mouthpiece, said tower member having an outer body which defines an interior volume;

an inner wall disposed in said outer body, said inner wall extending a substantial distance through said interior volume and defining a holding chamber interiorly of said inner wall, said inner wall and said outer body defining an air passage therebetween;

an inlet port disposed in said tower member for receiving a medicated aerosol from an exterior source into said holding chamber, an air inlet port disposed in said tower member for receiving air into said air passage; and an adapter disposed in said medicated aerosol inlet port, said adapter comprising a universal fitting which is capable of attaching said tower member to either a nebulizer or a metered dose inhaler (MDI);

wherein the air in said air passage flows therethrough around said inner wall and into said holding chamber, to be entrained with said medicated aerosol.

38. An aerosol enhancement device, comprising:

a mouthpiece;

a tower member fluidly attached to said mouthpiece, said tower member having an outer body having a total length and which defines an interior volume;

an inner wall disposed in said outer body, said inner wall extending more than half of said total length through said interior volume and defining a holding chamber inferiorly of said inner wall, said inner wall and said outer body defining an air passage therebetween;

an inlet port disposed in said tower member for receiving a medicated aerosol from an exterior source into said holding chamber;

an air inlet port disposed in said tower member for receiving air into said air passage;

wherein the air in said air passage flows therethrough around said inner wall and into said holding chamber, to be entrained with said medicated aerosol.

39. An aerosol enhancement device, comprising:

a mouthpiece;

a tower member fluidly attached to said mouthpiece, said tower member having an outer body which defines an interior volume;

an inner wall disposed in said outer body, said inner wall extending a substantial distance through said interior volume and defining a holding chamber interiorly of said inner wall, said inner wall and said outer body defining an air passage therebetween;

an inlet port disposed in said tower member for receiving a medicated aerosol from an exterior source into said holding chamber;

an air inlet port disposed in said tower member for receiving air into said air passage;

wherein the air in said air passage flows therethrough around said inner wall, into said holding chamber, to be entrained with said medicated aerosol, and then through an outlet from an upper end of said holding chamber;

said air inlet port and said holding chamber outlet having a barrier disposed therebetween, so that there is no fluid flow communication therebetween.

\* \* \* \* \*

UNITED STATES PATENT AND TRADEMARK OFFICE
CERTIFICATE OF CORRECTION

PATENT NO. : 6,363,932 B1
DATED : April 2, 2002
INVENTOR(S) : Forchione et al.

It is certified that error appears in the above-identified patent and that said Letters Patent is hereby corrected as shown below:

Column 8,
Line 25, change "20" to -- 19 --.

Column 9,
Line 30, after "claim" change "21" to -- 27 --.

Signed and Sealed this

Twenty-first Day of September, 2004

JON W. DUDAS
*Director of the United States Patent and Trademark Office*